(12) United States Patent
Shinoda et al.

(10) Patent No.: US 8,552,088 B2
(45) Date of Patent: Oct. 8, 2013

(54) CEMENT FOR DENTAL APPLICATIONS

(75) Inventors: Hiroki Shinoda, Chiyoda-ku (JP);
Mitsuru Takei, Kurashiki (JP); Hidemi Nakayama, Kurashiki (JP)

(73) Assignee: Kuraray Noritake Dental Inc., Kurashiki-shi (JP)

( * ) Notice: Subject to any disclaimer, the term of this patent is extended or adjusted under 35 U.S.C. 154(b) by 367 days.

(21) Appl. No.: 12/810,081

(22) PCT Filed: Dec. 25, 2008

(86) PCT No.: PCT/JP2008/073601
§ 371 (c)(1),
(2), (4) Date: Jun. 22, 2010

(87) PCT Pub. No.: WO2009/084586
PCT Pub. Date: Jul. 9, 2009

(65) Prior Publication Data
US 2010/0267856 A1    Oct. 21, 2010

(30) Foreign Application Priority Data
Dec. 28, 2007 (JP) ................................. 2007-340589

(51) Int. Cl.
| | |
|---|---|
| *A61K 6/08* | (2006.01) |
| *A61K 6/083* | (2006.01) |
| *A61K 6/06* | (2006.01) |
| *C08F 2/50* | (2006.01) |
| *C08J 3/28* | (2006.01) |

(52) U.S. Cl.
USPC ........... 523/116; 523/115; 523/113; 523/112; 523/117; 522/74; 522/77; 522/78; 522/79; 522/81; 522/173; 522/178; 522/182; 522/908

(58) Field of Classification Search
USPC ............. 522/74, 77, 78, 79, 81, 83, 173, 178, 522/182, 908; 523/105, 109, 111, 112, 113, 523/115, 116, 118, 117
See application file for complete search history.

(56) References Cited

U.S. PATENT DOCUMENTS

| | | | |
|---|---|---|---|
| 7,214,726 B2 * | 5/2007 | Qian | 523/116 |
| 2004/0077746 A1 | 4/2004 | Takeshita et al. | |
| 2004/0110864 A1 | 6/2004 | Hecht et al. | |
| 2004/0235981 A1 | 11/2004 | Qian | |
| 2005/0014861 A1 * | 1/2005 | Qian | 523/116 |
| 2006/0004122 A1 | 1/2006 | Hecht et al. | |
| 2006/0247330 A1 | 11/2006 | Takano et al. | |
| 2008/0015279 A1 * | 1/2008 | Tokui et al. | 522/182 |
| 2009/0048364 A1 * | 2/2009 | Liu | 522/48 |

FOREIGN PATENT DOCUMENTS

| | | |
|---|---|---|
| JP | 05-170619 | 7/1993 |
| JP | 09-067222 | 3/1997 |
| JP | 2004-529946 | 9/2004 |
| JP | 2005/8622 | 1/2005 |
| JP | 2006-299201 | 11/2006 |
| JP | 2008-19183 | 1/2008 |
| WO | 03/057180 | 7/2003 |

* cited by examiner

*Primary Examiner* — Sanza McClendon
(74) *Attorney, Agent, or Firm* — Oblon, Spivak, McClelland, Maier & Neustadt, L.L.P.

(57) ABSTRACT

A cement for dental use, containing a first agent and a second agent, wherein both of the first agent and the second agent contain a polymerizable monomer (a) and a filler (b), wherein the first agent and/or the second agent further contains a photopolymerization initiator (c), wherein further as a chemical polymerization initiator (d), either one of the first agent and the second agent contains an oxidizing agent (f) and the other contains a reducing agent (g), the oxidizing agent (f) and the reducing agent (g) constituting a redox polymerization initiator, wherein the photopolymerization initiator (c) contains an α-diketone, and the photopolymerization initiator (c) is contained in a total amount of from 0.010 to 0.100 parts by weight, based on 100 parts by weight of the total amount of the polymerizable monomer (a), wherein the chemical polymerization initiator (d) is contained in a total amount of from 0.001 to 20 parts by weight, based on 100 parts by weight of the total amount of the polymerizable monomer (a), and wherein a cured product has a compression modulus immediately after photocuring of from 100 to 400 MPa, and a compression modulus after 24 hours from photocuring of 500 MPa or more. The cement for dental use of the present invention is suitably used for adhering the dentine and a crowning restorative material in the field of dental therapy, or the like.

18 Claims, No Drawings

CEMENT FOR DENTAL APPLICATIONS

TECHNICAL FIELD

The present invention relates to a cement for dental use. More specifically, the present invention relates to a cement for dental use having excellent removability for an excess cement pushed out from a marginal part upon bonding the dentine and a crowning restorative material to be removed in a semi-cured state by provisional irradiation with a photoirradiation device.

BACKGROUND ART

Teeth that have lost functions due to caries or an accident or the like are restored by fixing a crowning restorative material made of a metal or ceramics, so-called inlay or crown, to the teeth, and an adhesive agent called a cement for dental use has been used in the fixation of the crowning restorative material to the teeth. Usually, upon adherence of the dentine and a crowning restorative material with a cement for dental use, a cement for dental use is applied in a slight excess amount to an inner wall side of the crowning restorative material to be pressed against the dentine. During this pressing procedure, a method including the steps of allowing an excess of a cement for dental use to be pushed out from a bonding part of the dentine and a crowning restorative material (hereinafter also referred to as a marginal part), and removing the pushed-out excess cement is employed. Therefore, the cement for dental use is provided as a paste-like composition having a high fluidity in a manner that the cement can be easily applied to the crowning restorative material and the excess cement is appropriately pushed out from the marginal part. In addition, unless the excess cement is completely removed, not only it is poor in esthetic appreciation but pushed-out and cured cement has a possibility of damaging the tissues in the oral cavity. Usually, this excess cement is removed by using a dental probe, or the like; however, it is difficult to remove the cement with the probe when the cement is in a state of high fluidity without being cured at all. Therefore, the removal of the excess cement is performed in a state in which the cement is in a completely cured state or in a state that the curing is progressed so that the fluidity is lost to a certain extent (semi-cured state).

Cements for dental use are classified into plural kinds depending upon the components and curing style, such as glass ionomer cement, resin-modified glass ionomer cement, and resin cement, each of which is actually used.

A glass ionomer cement is composed of a powder that elutes polyvalent metal ions and an aqueous solution of a polycarboxylic acid, and the cement is cured by chelate-crosslinking of the eluted polyvalent metal ions and the polycarboxylic acid upon mixing this powder and the aqueous solution. The cement takes a simple procedure because a pretreatment of the dentine is generally unnecessary, and has the feature that has excellent removability of an excess cement. However, the reason why the glass ionomer-cement has excellent removability of an excess cement is in that mechanical strength of the completely cured cement is low as compared to that of the resin cement, thereby making it possible to easily breakdown the cured-cement upon the removal of the cement using a probe. Therefore, while the glass ionomer cement has the advantages mentioned above, the cement has a disadvantage in the aspect of durability (reliability) of the cement itself. Further, the glass ionomer cement has a disadvantage that its physical properties such as mechanical strength lower upon contact with water such as saliva during curing are lowered.

In order to overcome the disadvantages owned by the glass ionomer cement, in the recent years, a cement for dental use called a resin-modified glass ionomer cement in which a radical-polymerizable monomer and a chemical polymerization initiator are blended, in addition to a polycarboxylic acid, is developed and made available to the market. The cement has improved mechanical strength, which has been a disadvantage in the glass ionomer cement, by curing according to radical-polymerization in addition to curing according to chelate-crosslinking, thereby allowing the polymer of the radical-polymerizable monomers to be present in the resulting cured product. However, the resin-modified glass ionomer cement as described above is no different in the aspect that the cured product is mainly made of a polycarboxylic acid and a chelating compound of a polyvalent metal ion (ionomer), so that the cement has a low mechanical strength and insufficient reliability, as compared to the resin cement mainly made of the polymer of the radical-polymerizable monomers. In addition, recently, a resin-modified glass ionomer cement, which is mainly made of a polymer of radical-polymerizable monomers, having a mechanical strength even more closer to that of a resin cement is used for practical purposes; however, the cement for dental use as described above has some disadvantages that a time period in a semi-cured state is so short that timing for removing the cement is made difficult, and that the mechanical strength becomes too high if completely cured, so that it is very difficult to remove the cement, as in the same manner as the resin cement described later.

Among the cements for dental use, a resin cement is composed of a composition containing a radical-polymerizable monomer, an inorganic or organic filler, and a chemical polymerization initiator, in which curing is carried out by radical polymerization. In addition, since a radical-polymerizable monomer containing an acidic group is blended as a part of the radical-polymerizable monomers, the resin cement shows a firm adhesion to the dentine and various metals.

Also, a resin cement in which an inorganic filler is mainly blended as a filler has even more excellent mechanical strength and durability. In the cement having a high mechanical strength as described above, since it is difficult to remove an excess cement after the cement is completely cured, the removal of an excess cement is carried out in a semi-cured state. However, a chemical polymerization initiator is blended in the cement in an amount that enables complete curing of the cement, so that there is a disadvantage that a time period for which the cement is in a semi-cured state is short, thereby making the timing for removing the cement difficult.

On the other hand, in a resin cement blended mainly with an organic filler as a filler, a cement cured product becomes undesirably elastic, so that it is again difficult to remove the cement with a probe after being completely cured. Therefore, the removal of an excess cement is carried out in a semi-cured state; however, there is a disadvantage that a time period for which the cement is in a semi-cured state is short, thereby making the timing of removing an excess cement difficult, as in the same manner as that blended with an inorganic filler.

Furthermore, in a resin cement being valued of its high bond strength against the dentine or a crowning restorative material, regardless of using an inorganic filler or an organic filler, if an excess cement that is deposited to sites other than a desired site is undesirably completely cured and firmly adhered, it is very difficult to remove the cured product.

On the other hand, in a cement for dental use in which radical-polymerizable monomers for a resin cement or the like are main curing components, techniques of adjusting a chemical curing time, thereby improving removability of an excess cement in chemical curing have been disclosed.

For example, Patent Publication 1 discloses a technique of delaying a curing time by adding a polymerization inhibitor, and Patent Publication 2 discloses a technique of improving removability of an excess cement in chemical curing by blending a styrenic derivative having a specified structure, thereby extending an operating time from the beginning of curing to the termination of curing.

On the other hand, in the recent years, in a cement for dental use in which radical-polymerizable monomers for a resin cement or the like are main curing components, a dual curing material having both photocuring and chemical curing properties, the dual curing material containing a photopolymerization initiator in addition to a chemical polymerization initiator, is widely used (Patent Publication 3).

Patent Publication 1: Japanese Patent Laid-Open No. Hei 9-67222
Patent Publication 2: WO 2003/057180
Patent Publication 3: Japanese Unexamined Patent Publication No. 2004-529946

DISCLOSURE OF THE INVENTION

Problems to be Solved by the Invention

However, in a case where a curing time is delayed using a polymerization inhibitor in reference to Patent Publication 1, once the polymerization inhibitor is completely consumed for the delaying of the polymerization time and disappears, the polymerization reaction would be progressed at a stroke, so that it would no way sufficiently satisfy in the aspect of extension of the timing of removing an excess cement. In addition, a disadvantage such as lowering of bond strength against the dentine in accordance with an amount of increase in the inhibitor may arise in some cases.

Even when a styrenic derivative having a specified structure is used in reference to Patent Publication 2, although an operating time can be extended, the timing for removing an excess cement cannot be adjusted, so that it cannot sufficiently satisfy for clinical purposes.

In a dual-curing type in which both photocuring and chemical curing are carried out as described in Patent Publication 3, since the rate of polymerization and curing by photoirradiation is markedly faster, it is difficult to control the time period for photoirradiation to provide an appropriate semi-cured state; therefore, there may be a disadvantage that if an excess cement would be undesirably progressed too far in curing and firmly adhered, the removal of the excess cement would be very difficult.

An object of the present invention is to provide a cement for dental use, having excellent mechanical strength and removability of an excess cement.

Means to Solve the Problems

As a result of intensive studies remarking on removability upon removing an excess cement by photoirradiation in a semi-cured state and mechanical properties of a cement for dental use, the present inventors have found that a composition having excellent removability of excess cement after photoirradiation and at the same time excellent mechanical strength demanded as a cement for dental use is obtained in a case where the amount of the photopolymerization initiator and the content of the chemical polymerization initiator are each within a specified range. The present invention has been perfected thereby.

Specifically, the present invention relates to:

[1] a cement for dental use, containing a first agent and a second agent, wherein both of the first agent and the second agent contain a polymerizable monomer (a) and a filler (b), wherein the first agent and/or the second agent further contains a photopolymerization initiator (c), wherein further as a chemical polymerization initiator (d), either one of the first agent and the second agent contains an oxidizing agent (f) and the other contains a reducing agent (g), the oxidizing agent (f) and the reducing agent (g) constituting a redox polymerization initiator,
wherein the photopolymerization initiator (c) contains an α-diketone, and the photopolymerization initiator (c) is contained in a total amount of from 0.010 to 0.100 parts by weight, based on 100 parts by weight of the total amount of the polymerizable monomer (a),
wherein the chemical polymerization initiator (d) is contained in a total amount of from 0.001 to 20 parts by weight, based on 100 parts by weight of the total amount of the polymerizable monomer (a), and
wherein a cured product has a compression modulus immediately after photocuring of from 100 to 400 MPa, and a compression modulus after 24 hours from photocuring of 500 MPa or more;

[2] the cement for dental use according to the above [1], wherein the polymerizable monomer (a) is a polymerizable monomer having a (meth)acryl group and/or a (meth)acrylamide group as a polymerizable group;

[3] the cement for dental use according to the above [1] or [2], wherein a ratio of a total weight of the photopolymerization initiator (c) to a total weight of the chemical polymerization initiator (d) [photopolymerization initiator (c)/chemical polymerization initiator (d)] is from 1/28 to 1/5;

[4] the cement for dental use according to any one of the above [1] to [3], further containing a polymerization accelerator (e) in an amount of from 0.001 to 20 parts by weight, based on 100 parts by weight of a total amount of the polymerizable monomer (a);

[5] the cement for dental use according to the above [4], wherein the polymerization accelerator (e) is at least one compound selected from the group consisting of ethyl 4-N,N-dimethylaminobenzoate ester, methyl 4-N,N-dimethylaminobenzoate ester, n-butoxyethyl N,N-dimethylaminobenzoate ester, 4-N,N-dimethylaminobenzophenone, sodium benzenesulfinate, sodium p-toluenesulfinate, sodium 2,4,6-triisopropylbenzenesulfinate, sodium sulfite, potassium sulfite, calcium sulfite, ammonium sulfite, sodium hydrogensulfite, and potassium hydrogensulfite; and

[6] the cement for dental use according to any one of the above [1] to [5], wherein the first agent is a first paste (A), and the second agent is a second paste (B).

Effects of the Invention

The cement for dental use of the present invention satisfies both removability upon removing an excess cement by photoirradiation in a semi-cured state and mechanical properties demanded for a cement for dental use.

BEST MODE FOR CARRYING OUT THE INVENTION

The cement for dental use of the present invention is a cement for dental use containing a polymerizable monomer (a), a filler (b), a photopolymerization initiator (c), and a chemical polymerization initiator (d), and more specifically a cement for dental use containing a first agent and a second agent, wherein both of the first agent and the second agent contain a polymerizable monomer (a) and a filler (b), wherein the first agent and/or the second agent further contains a photopolymerization initiator (c), wherein further as a chemical polymerization initiator (d), either one of the first agent and the second agent contains an oxidizing agent (f) and the other contains a reducing agent (g), the oxidizing agent (f) and the reducing agent (g) constituting a redox polymerization initiator.

In the present invention, in the above constitution, the great features reside in that the photopolymerization initiator (c) is contained in a total amount of from 0.010 to 0.100 parts by weight, based on 100 parts by weight of the total amount of the polymerizable monomer (a), and that the chemical polymerization initiator (d) is contained in a total amount of from 0.001 to 20 parts by weight, based on 100 parts by weight of the total amount of the polymerizable monomer (a). The phrase "contained in an amount" as used herein means "content" and/or "blended amount."

A conventional cement for dental use contains a photopolymerization initiator in an amount of from 0.2 to 1 part by weight, based on a total amount 100 parts by weight of the polymerizable monomers. However, in the present invention, a photopolymerization initiator is contained in a total amount of from 0.010 to 0.100 parts by weight, based on 100 parts by weight of a total amount of the polymerizable monomers, which is lower than that of the conventional product, and at the same time a chemical polymerization initiator is contained in an amount of from 0.001 to 20 parts by weight, based on 100 parts by weight of a total amount of the polymerizable monomers, whereby surprisingly finding that both removability of an excess cement and mechanical strength as a cement for dental use can be satisfied in a well balanced manner.

The cement for dental use of the present invention contains a first agent and a second agent, the cement containing a polymerizable monomer (a), a filler (b), a photopolymerization initiator (c), and a chemical polymerization initiator (d).

The polymerizable monomer (a) is necessary as a component for a paste-like cement for dental use, and is polymerized by the progress of a polymerization reaction with a polymerization initiator, so that the polymerizable monomer is contained in both the first agent and the second agent. The polymerizable monomer (a) is preferably a radical-polymerizable monomer having a polymerizable group, and the polymerizable group is preferably a (meth)acryl group and/or a (meth)acrylamide group, from the viewpoint of easiness in radical polymerization. The cement for dental use of the present invention is used in an oral cavity, and the oral cavity is a wet environment so that there is a risk that a polymerizable group may be detached by hydrolysis or the like. Therefore, the polymerizable group is preferably a methacryl group and/or a methacrylamide group, when irritability of the detached polymerizable group to a living body is taken into consideration. The term "(meth)acryl" as used herein means acryl and methacryl, and the term "(meth)acryloyl" means acryloyl and methacryloyl.

In the present invention, the polymerizable monomer (a) is exemplified by a polyfunctional monomer having a plurality of the following polymerizable groups, and a monofunctional monomer having one of the following polymerizable groups.

The polyfunctional monomer includes bifunctional polymerizable monomers of aromatic compounds, bifunctional polymerizable monomers of aliphatic compounds, trifunctional or higher polyfunctional polymerizable monomers, and the like.

Examples of the bifunctional polymerizable monomers of aromatic compounds include 2,2-bis((meth)acryloyloxyphenyl)propane, 2,2-bis[4-(3-(meth)acryloyloxy)-2-hydroxypropoxyphenyl]propane (generally referred to as "Bis-GMA"), 2,2-bis(4-(meth)acryloyloxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxydiethoxyphenyl)propane, 2-(4-(meth)acryloyloxydiethoxyphenyl)-2-(4-(meth)acryloyloxy ditriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, 2,2-bis(4-(meth)acryloyloxyisopropoxyphenyl)propane, 1,4-bis(2-(meth)acryloyloxyethyl)pyromyritate, and the like. Among them, 2,2-bis[4-(3-(meth)acryloyloxy)-2-hydroxypropoxyphenyl]propane and 2,2-bis(4-(meth)acryloyloxypolyethoxyphenyl)propane are preferred, from the aspect of a large mechanical strength of the resulting cement for dental use. Here, among the 2,2-bis(4-(meth)acryloyloxypolyethoxyphenyl)propane, compounds of which ethoxy group has an average number of moles of 2.6 (generally referred to as "D2.6E") are preferred.

Examples of the bifunctional polymerizable monomers of the aliphatic compounds include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 1,2-bis(3-methacryloyloxy-2-hydroxypropoxy)ethane, 2,2,4-trimethylhexamethylenebis(2-carbamoyloxyethyl) dimethacrylate (generally referred to as "UDMA"), 1,2-bis(3-methacryloyloxy-2-hydroxypropyloxy)ethane, and the like. Among them, glycerol di(meth)acrylate, triethylene glycol di(meth)acrylate, neopentyl glycol di(meth)acrylate, 2,2,4-trimethylhexamethylenebis(2-carbamoyloxyethyl) dimethacrylate and 1,2-bis(3-methacryloyloxy-2-hydroxypropyloxy)ethane are preferred, from the viewpoint of excellent handling property of the resulting cement for dental use.

Examples of the trifunctional or higher polyfunctional polymerizable monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol penta(meth)acrylate, N,N-(2,2,4-trimethylhexamethylene)bis[2-(aminocarboxy)propane-1,3-diol]tetramethacrylate, 1,7-diacryloyloxy-2,2,6,6-tetraacryloyloxymethyl-4-oxyheptane, and the like. Among them, N,N-(2,2,4-trimethylhexamethylene)bis[2-(aminocarboxy)propane-1,3-diol]tetramethacrylate is preferred, from the aspect that the resulting cement for dental use has a large mechanical strength.

Examples of the monofunctional monomer include 2-hydroxyethyl (meth)acrylate, 3-hydroxypropyl (meth)acrylate, 4-hydroxybutyl (meth)acrylate, 6-hydroxyhexyl (meth)acrylate, 10-hydroxydecyl (meth)acrylate, propylene glycol mono(meth)acrylate, glycerol mono(meth)acrylate, erythritol mono(meth)acrylate, N-methylol (meth)acrylamide, N-hydroxyethyl (meth)acrylamide, N,N-(dihydroxyethyl) (meth)acrylamide, methyl (meth)acrylate, ethyl (meth)acrylate, propyl (meth)acrylate, isopropyl (meth)acrylate, butyl (meth)acrylate, isobutyl (meth)acrylate, benzyl (meth)acrylate, lauryl (meth)acrylate, 2,3-dibromopropyl (meth)acrylate, 3-(meth)acryloyloxypropyl trimethoxysilane, 11-(meth)acryloyloxyundecyl trimethoxysilane, (meth)acrylamide, and the like. Among them, 2-hydroxyethyl (meth)acrylate, 3-hydroxypropyl (meth)acrylate, glycerol mono(meth)acrylate and erythritol mono(meth)acrylate are preferred, from the aspect of having a high affinity and a large bond strength of the resulting cement for dental use with the dentine.

In addition, the cement for dental use of the present invention may contain a polymerizable monomer containing an acidic group as the polymerizable monomer (a), from the viewpoint of having excellent bond strength against the dentine or a prosthetic for dental use. The polymerizable monomer containing an acidic group as described above includes a radical-polymerizable monomer having at least one acidic group such as a phosphoric acid group, a pyrophosphoric acid group, a thiophosphoric acid group, a phosphonic acid group, a sulfonic acid group, or a carboxylic acid group, and a polymerizable group.

Examples of the polymerizable monomers having a phosphoric acid group are, for example, 2-(meth)acryloyloxyethyl dihydrogenphosphate, 3-(meth)acryloyloxypropyl dihydrogenphosphate, 4-(meth)acryloyloxybutyl dihydrogenphosphate, 5-(meth)acryloyloxypentyl dihydrogenphosphate, 6-(meth)acryloyloxyhexyl dihydrogenphosphate, 7-(meth)acryloyloxyheptyl dihydrogenphosphate, 8-(meth)acryloyloxyoctyl dihydrogenphosphate, 9-(meth)acryloyloxynonyl dihydrogenphosphate, 10-(meth)acryloyloxydecyl dihydrogenphosphate, 11-(meth)acryloyloxyundecyl dihydrogenphosphate, 12-(meth)acryloyloxydodecyl dihydrogenphosphate, 16-(meth)acryloyloxyhexadecyl dihydrogenphosphate, 20-(meth)acryloyloxyeicosyl dihydrogenphosphate, bis[2-(meth)acryloyloxyethyl]hydrogenphosphate, bis[4-(meth)acryloyloxybutyl]hydrogenphosphate, bis[6-(meth)acryloyloxyhexyl]hydrogenphosphate, bis[8-(meth)acryloyloxyoctyl]hydrogenphosphate, bis[9-(meth)acryloyloxynonyl]hydrogenphosphate, bis[10-(meth)acryloyloxydecyl]hydrogenphosphate, 1,3-di(meth)acryloyloxypropyl dihydrogenphosphate, 2-(meth)acryloyloxyethylphenyl hydrogenphosphate, 2-(meth)acryloyloxyethyl-2-bromoethyl hydrogenphosphate, bis[2-(meth)acryloyloxy-(1-hydroxymethypethyl] hydrogenphosphate, and acid chlorides thereof, alkali metal salts thereof, ammonium salts thereof, and the like.

Examples of the polymerizable monomer having a pyrophosphoric acid group are, for example, bis[2-(meth)acryloyloxyethyl]pyrophosphate, bis[4-(meth)acryloyloxybutyl]pyrophosphate, bis[6-(meth)acryloyloxyhexyl]pyrophosphate, bis[8-(meth)acryloyloxyoctyl]pyrophosphate, bis[10-(meth)acryloyloxydecyl]pyrophosphate, and acid chlorides thereof, alkali metal salts thereof, ammonium salts thereof, and the like.

Examples of the polymerizable monomer having a thiophosphoric acid group are, for example, 2-(meth)acryloyloxyethyl dihydrogenthiophosphate, 3-(meth)acryloyloxypropyl dihydrogenthiophosphate, 4-(meth)acryloyloxybutyl dihydrogenthiophosphate, 5-(meth)acryloyloxypentyl dihydrogenthiophosphate, 6-(meth)acryloyloxyhexyl dihydrogenthiophosphate, 7-(meth)acryloyloxyheptyl dihydrogenthiophosphate, 8-(meth)acryloyloxyoctyl dihydrogenthiophosphate, 9-(meth)acryloyloxynonyl dihydrogenthiophosphate, 10-(meth)acryloyloxydecyl dihydrogenthiophosphate, 11-(meth)acryloyloxyundecyl dihydrogenthiophosphate, 12-(meth)acryloyloxydodecyl dihydrogenthiophosphate, 16-(meth)acryloyloxyhexadecyl dihydrogenthiophosphate, 20-(meth)acryloyloxyeicosyl dihydrogenthiophosphate, and acid chlorides thereof, alkali metal salts thereof, ammonium salts thereof, and the like.

Examples of the polymerizable monomer having a phosphonic acid group are, for example, 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, 10-(meth)acryloyloxydecyl-3-phosphonoacetate, and acid chlorides thereof, alkali metal salts thereof, ammonium salts thereof, and the like.

Examples of the polymerizable monomer having a sulfonic acid group include 2-(meth)acrylamide-2-methylpropanesulfonic acid, styrenesulfonic acid, 2-sulfoethyl (meth)acrylate, and the like.

Examples of the polymerizable monomer having a carboxylic acid group include polymerizable monomers having one carboxylic group in a molecule, and polymerizable monomers having plural carboxylic groups in a molecule.

Examples of the polymerizable monomers having one carboxylic group in a molecule include (meth)acrylic acid, N-(meth)acryloylglycine, N-(meth)acryloylaspartic acid, N-(meth)acryloyl-5-aminosalicylic acid, 0-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, and acid halides thereof, and the like.

Examples of the polymerizable monomers having plural carboxylic groups in a molecule include 2-(meth)acryloyloxyethyl hydrogensuccinate, 2-(meth)acryloyloxyethyl hydrogenphthalate, 2-(meth)acryloyloxyethyl hydrogenmalate, 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxyethyl trimellitate anhydride, 4-(meth) acryloyloxybutyl trimellitate, 4-(meth)acryloyloxyhexyl trimellitate, 4-(meth)acryloyloxydecyl trimellitate, 2-(meth)acryloyloxyethyl-3'-(meth)acryloyloxy-2'-(3,4-dicarboxybenzoyloxy)propyl succinate, and acid anhydrides thereof or acid halides thereof, and the like.

Among the polymerizable monomers containing an acidic group as listed above, the polymerizable monomers containing an acidic group preferably have a phosphoric acid group or a phosphonic acid group, and more preferably have a phosphoric acid group, from the viewpoint of excellent bond strength of the cement for dental use. Among them, the polymerizable monomers having an alkyl group or alkylene group of which main chain has 6 to 20 carbon atoms in a molecule are preferred, and those having an alkylene group of which main chain has 8 to 12 carbon atoms, such as 10-(meth)acryloyloxydecyl dihydrogenphosphate, in a molecule are more preferred.

The polymerizable monomer (a) mentioned above may be used alone, but it is preferable that the bifunctional polymerizable monomer of an aromatic compound is used together with the bifunctional polymerizable monomer of an aliphatic compound and/or the monofunctional monomer, from the viewpoint of mechanical strength, handling property, bond strength, curing property of the cement for dental use. When used together, the ratio thereof is not particularly limited. Supposing a case where a total amount of the polymerizable monomer (a) is 100 parts by weight, the amount of the bifunctional polymerizable monomer of the aromatic compound blended is preferably from 40 to 90 parts by weight, more preferably from 50 to 80 parts by weight, and even more preferably from 55 to 75 parts by weight.

In addition, the amount of the polymerizable monomer containing an acidic group blended is not particularly limited. Supposing a case where a total amount of the polymerizable monomer (a) is 100 parts by weight, the amount of the polymerizable monomer containing an acidic group blended is preferably from 1 to 60 parts by weight, more preferably from 2 to 50 parts by weight, and even more preferably from 5 to 40 parts by weight. If the amount of the polymerizable monomer containing an acidic group blended is 1 part by weight or more, excellent bond strength is obtained, and if the amount of the polymerizable monomer containing an acidic group blended is 60 parts by weight or less, polymerizability for the cement for dental use would be appropriate, and its bond strength would be excellently maintained.

The filler (b) is necessary for adjusting paste-like properties of the cement for dental use before curing, and increasing mechanical strength after curing, and the filler is contained in both the first agent and the second agent. The filler as described above includes organic fillers, inorganic fillers, organic-inorganic composite fillers, and the like.

The organic filler includes, for example, methyl polymethacrylate, ethyl polymethacrylate, methyl methacrylate-ethyl methacrylate copolymers, a crosslinked methyl polymethacrylate, a crosslinked ethyl polymethacrylate, polyamides, polyvinyl chloride, polystyrenes, chloroprene rubber, nitrile rubber, ethylene-vinyl acetate copolymers, styrene-butadiene copolymers, acrylonitrile-styrene copolymers, acrylonitrile-styrene-butadiene copolymers, and the like, and each of these organic fillers can be used alone or in a mixture of two or more kinds. The shape of the organic filler is not particularly limited, and the organic filler can be used by appropriately selecting the particle size of the filler.

The inorganic filler includes quartz, silica, alumina, silica-titania, silica-titania-barium oxide, silica-zirconia, silica-alumina, lanthanum glass, borosilicate glass, sodium glass, barium glass, strontium glass, glass ceramics, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, strontium calcium fluoroaluminosilicate glass, and the like. Each of these inorganic fillers can be used alone or in a mixture of two or more kinds. The shape of the inorganic filler is not particularly limited, and irregularly shaped fillers and spherical fillers or the like can be appropriately selected.

In order to adjust the fluidity of the composition, the above-mentioned inorganic filler may be used after previously surface-treating with a known surface treatment agent such as a silane coupling agent as needed. The surface treatment agent includes, for example, vinyltrimethoxysilane, vinyltriethoxysilane, vinyltrichlorosilane, vinyltri(β-methoxyethoxy)silane, 3-methacryloyloxypropyl trimethoxysilane, 11-methacryloyloxyundecyl trimethoxysilane, 3-glycidoxypropyl trimethoxysilane, 3-mercaptopropyl trimethoxysilane, 3-aminopropyl triethoxysilane, and the like.

As a method for surface treatment, a known method can be used without particular limitations. The method for surface treatment includes, for example, a method including the step of spray-adding the above-mentioned surface treatment agent while vigorously stirring an inorganic filler; a method including the steps of dispersing or dissolving an inorganic filler and the above-mentioned surface treatment agent in an appropriate solvent, and removing the solvent; alternatively, a method including the steps of hydrolyzing an alkoxy group of the above-mentioned surface treatment agent in an aqueous solution in the presence of an acid catalyst to convert to a silanol group, adhering the silanol group on an inorganic filler surface in the aqueous solution, and removing water therefrom; and the like. In any of the methods, the surface treatment can be carried out by heating usually in a range of from 50° to 150° C., and completing the reaction of the surface of an inorganic filler with the above-mentioned surface treatment agent.

The organic-inorganic composite filler refers to a filler obtained by previously adding a polymerizable monomer to the above-mentioned inorganic filler to form into a paste-like state, polymerizing the components, and pulverizing the reaction mixture. As the organic-inorganic composite fillers, for example, TMPT filler (a product obtained by blending trimethylolpropane methacrylate and a silica filler, and polymerizing the components, and pulverizing the reaction mixture) or the like can be used. The shape of the above-mentioned organic-inorganic composite filler is not particularly limited, and the composite filler can be used by appropriately selecting a particle size of the filler.

The average particle size of the filler (b) is preferably from 0.001 to 50 µm, and more preferably from 0.001 to 10 µm, from the viewpoint of handling property and mechanical strength of the resulting cement for dental use. The average particle size of the filler as used herein can be measured by any known methods for one of ordinary skill in the art; for example, the average particle size can be easily measured by a laser diffraction particle size distribution analyzer described in Examples set forth below.

The amount of the filler (b) blended is not particularly limited. The amount of the filler (b) blended is preferably from 100 to 900 parts by weight, more preferably from 130 to 600 parts by weight, and even more preferably from 150 to 400 parts by weight, based on 100 parts by weight of a total amount of the polymerizable monomer (a), from the viewpoint of handling property and mechanical strength of the resulting cement for dental use. If the amount of the filler (b) contained is 100 parts by weight or more, the cured product has excellent mechanical strength, and if the amount of the filler contained is 900 parts by weight or less, the fluidity of the cement for dental use is at an appropriate level, so that sufficient blending can be carried out, whereby there is no risk of lowering the strength of the cured product.

The photopolymerization initiator (c) is necessary for allowing the cement for dental use to begin the polymerization by photoirradiation, and the photopolymerization initiator (c) is contained in the first agent and/or the second agent mentioned above. One of the features of the present invention is in the use of an α-diketone as these photopolymerization initiators.

By the use of the α-diketone, a cement for dental use having excellent photocuring properties in visible and near ultraviolet regions, and showing sufficient photocuring properties even when using any of the light sources such as a halogen lamp, a light-emitting diode (LED), or a xenon lamp is obtained.

The α-diketone includes, for example, diacetyl, dibenzyl, camphorquinone, 2,3-pentadione, 2,3-octadione, 9,10-phenanthrenequinone, 4,4'-oxybenzyl, acenaphthenequinone, and the like. Among them, camphorquinone is preferred, from the viewpoint of having a maximum absorption wavelength in the visible light region.

In addition, in the present invention, a photopolymerization initiator such as a (bis)acyl phosphine oxide and a salt thereof, a water-soluble acyl phosphine oxide, a thioxanthone or a quaternary ammonium salt of a thioxanthone, a ketal, a coumarin, an anthraquinone, a benzoin alkyl ether, and an α-aminoketone (hereinafter also referred to as a photopolymerization initiator other than the α-diketone) may be used together with the α-diketone, to an extent that would not impair the effects of the present invention.

Among the (bis)acyl phosphine oxides, acyl phosphine oxides include 2,4,6-trimethylbenzoyl diphenyl phosphine oxide, 2,6-dimethoxybenzoyl diphenyl phosphine oxide, 2,6-dichlorobenzoyl diphenyl phosphine oxide, 2,4,6-trimethylbenzoyl methoxyphenyl phosphine oxide, 2,4,6-trimethylbenzoyl ethoxyphenyl phosphine oxide, 2,3,5,6-tetramethylbenzoyl diphenyl phosphine oxide, benzoyl di-(2,6-dimethylphenyl) phosphonate, and the like. Bis acyl phosphine oxides include bis-(2,6-dichlorobenzoyl)phenyl phosphine oxide, bis-(2,6-dichlorobenzoyl)-2,5-dimethylphenyl phosphine oxide, bis-(2,6-dichlorobenzoyl)-4-propylphenyl phosphine oxide, bis-(2,6-dichlorobenzoyl)-1-naphthyl phosphine oxide, bis-(2,6-dimethoxybenzoyl) phenyl phosphine oxide, bis-(2,6-dimethoxybenzoyl)-2,4,4-trimethylpentyl phosphine oxide, bis-(2,6-dimethoxybenzoyl)-2,5-dimethylphenyl phosphine oxide, bis-(2,4,6-trimethylbenzoyl)phenyl phosphine oxide, (2,5,6-trimethylbenzoyl)-2,4,4-trimethylpentyl phosphine oxide, and the like. In addition, the salts of the (bis)acyl phosphine oxides are not particularly limited, and include known salts.

The water-soluble acyl phosphine oxide preferably has an alkali metal ion, an alkaline earth metal ion, a pyridinium ion, or an ammonium ion in the acyl phosphine oxide molecule. For example, the water-soluble acyl phosphine oxide can be synthesized in accordance with the methods disclosed in European Patent No. 0009348 or Japanese Patent Laid-Open No. Sho-57-197289.

Specific examples of the above water-soluble acyl phosphine oxide include monomethyl acetyl phosphonate sodium, monomethyl (1-oxopropyl)phosphonate sodium, monomethyl benzoyl phosphonate sodium, monomethyl (1-oxobutyl)phosphonate sodium, monomethyl (2-methyl-1-oxopropyl)phosphonate sodium, acetyl phosphonate sodium, monomethyl acetyl phosphonate sodium, acetyl methyl phosphonate sodium, methyl 4-(hydroxymethoxyphosphinyl)-4-oxobutanoate sodium, monosodium methyl-4-oxophosphonobutanoate, sodium acetyl phenyl phosphinate, sodium (1-oxopropyl)pentyl phosphinate, sodium methyl-4-(hydroxypentylphosphinyl)-4-oxobutanoate, acetyl pentyl phosphinate sodium, acetyl ethyl phosphinate sodium, methyl (1,1-dimethyl)methyl phosphinate sodium, (1,1-diethoxyethyl)methyl phosphinate sodium, (1,1-diethoxyethyl)methyl phosphinate sodium, lithium methyl-4-(hydroxymethylphosphinyl)-4-oxobutanoate, 4-(hydroxymethylphosphinyl)-4-oxobutanoic acid dilithium, sodium methyl(2-methyl-1,3-dioxolan-2-yl) phosphinate, sodium methyl (2-methyl-1,3-thiazolidin-2-yl) phosphinate, sodium (2-methylperhydro-1,3-diazin-2-yl) phosphinate, sodium acetyl phosphinate, sodium (1,1-diethoxyethyl) phosphinate, sodium (1,1-diethoxyethyl)methyl phosphinate, sodium methyl (2-methyloxathiolan-2-yl) phosphinate, sodium methyl (2,4,5-trimethyl-1,3-dioxolan-2-yl) phosphinate, sodium methyl (1,1-propoxyethyl) phosphinate, sodium (1-methoxyvinyl) methyl phosphinate, sodium (1-ethylthiovinyl) methyl phosphinate, sodium methyl (2-methylperhydro-1,3-diazin-2-yl) phosphinate, sodium methyl (2-methylperhydro-1,3-thiazin-2-yl) phosphinate, sodium methyl (2-methyl-1,3-diazolidin-2-yl) phosphinate, sodium methyl (2-methyl-1,3-thiazolidin-2-yl) phosphinate, sodium (2,2-dicyano-1-methylethynyl) phosphinate, sodium acetyl methyl phosphinate oxime, sodium acetyl methyl phosphinate-O-benzyloxime, sodium 1-[(N-ethoxyimino)ethyl]methyl phosphinate, sodium methyl (1-phenyliminoethyl) phosphinate, sodium methyl (1-phenylhydrazone ethyl) phosphinate, sodium [-(2,4-dinitrophenylhydrazono)ethyl]methyl phosphinate, sodium acetyl methyl phosphinate semicarbazone, sodium (1-cyano-1-hydroxyethyl) methyl phosphinate, sodium (dimethoxymethyl) methyl phosphinate, sodium formyl methyl phosphinate, sodium (1,1-dimethoxypropyl) methyl phosphinate, sodium methyl (1-oxopropyl) phosphinate, (1,1-dimethoxypropyl) methyl phosphinate dodecylguanidine, (1,1-dimethoxypropyl) methyl phosphinate isopropylamine, sodium acetyl methylphosphinate thiosemicarbazone, 1,3,5-tributyl-4-methylamino-1,2,4-triazolium (1,1-dimethoxyethyl)-methyl phosphinate, 1-butyl-4-butylaminomethylamino-3,5-dipropyl-1,2,4-triazolium (1,1-dimethoxyethyl)-methyl phosphinate, sodium 2,4,6-trimethylbenzoyl phenyl phosphine oxide, potassium 2,4,6-trimethylbenzoyl phenyl phosphine oxide, ammonium 2,4,6-trimethylbenzoyl phenyl phosphine oxide, and the like. Further, compounds listed in Japanese Patent Laid-Open No. 2000-159621 are also included.

Among these (bis)acyl phosphine oxides and water-soluble acyl phosphine oxides, 2,4,6-trimethylbenzoyl diphenyl phosphine oxide, 2,4,6-trimethylbenzoyl methoxyphenyl phosphine oxide, bis(2,4,6-trimethylbenzoyl) acyl phosphine oxide and sodium 2,4,6-trimethylbenzoyl phenyl phosphine oxide are preferred.

As the thioxanthone or the quaternary ammonium salt of the thioxanthone, for example, thioxanthone, 2-chlorothioxanthen-9-one, 2-hydroxy-3-(9-oxy-9H-thioxanthen-4-yloxy)-N,N,N-trimethyl-propane ammonium chloride, 2-hydroxy-3-(1-methyl-9-oxy-9H-thioxanthen-4-yloxy)-N,N,N-trimethyl-propane ammonium chloride, 2-hydroxy-3-(9-oxo-9H-thioxanthen-2-yloxy)-N,N,N-trimethyl-propane ammonium chloride, 2-hydroxy-3-(3,4-dimethyl-9-oxo-9H-thioxanthen-2-yloxy)-N,N,N-trimethyl-1-propane ammonium chloride, 2-hydroxy-3-(3,4-dimethyl-9H-thioxanthen-2-yloxy)-N,N,N-trimethyl-1-propane ammonium chloride, 2-hydroxy-3-(1,3,4-trimethyl-9-oxo-9H-thioxanthen-2-yloxy)-N,N,N-trimethyl-1-propane ammonium chloride, or the like can be used.

Among these thioxanthones or the quaternary ammonium salts of the thioxanthones, a preferred thioxanthone is 2-chlorothioxanthen-9-one, and a preferred quaternary ammonium salt of the thioxanthone is 2-hydroxy-3-(3,4-dimethyl-9H-thioxanthen-2-yloxy)-N,N,N-trimethyl-1-propane ammonium chloride.

Examples of the ketal include benzyl dimethyl ketal, benzyl diethyl ketal, and the like.

Examples of the coumarin compounds include compounds listed in Japanese Patent Laid-Open Nos. Hei-9-3109 and Hei-10-245525, such as 3,3'-carbonyl bis(7-diethylamino) coumarin, 3-(4-methoxybenzoyl)coumarin, 3-thienoyl coumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl) coumarin, 3-benzoyl-8-methoxycoumarin, 3,5-carbonylbis (7-methoxycoumarin), 3-benzoyl-6-bromocoumarin, 3,3'-carbonylbiscoumarin, 3-benzoyl-7-dimethylaminocoumarin, 3-benzoyl benzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetyl benzo[f]coumarin, 7-methoxy-3-(p-nitrobenzoyl)coumarin, 3-(p-nitrobenzoyl)coumarin, 3-benzoyl-8-methoxycoumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl) benzo[f] coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazole-2-ylidene)acetyl]coumarin, 3-[(1-methylnaphtho[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino) coumarin, 3,3-carbonylbis(7-dibutylaminocoumarin), 3,3'-carbonyl-7-diethylaminocoumarin-7'-bis(butoxyethyl) aminocoumarin, 10-[3-[4-(dimethylamino)phenyl]-1-oxo-2-propenyl]-2,3,6,7-1,1,7,7-tetramethyl 1H,5H,11H-Nbenzopyrano[6,7,8-ij]quinolidin-11-one, and 10-(2-benzothiazoyl)-2,3,6,7-tetrahydro-1,1,7,7-tetramethyl 1H,5H,11H-Mbenzopyrano[6,7,8-ij]quinolidin-11-one.

Examples of the anthraquinone include anthraquinone, 1-chloroanthraquinone, 2-chloroanthraquinone, 1-bromoanthraquinone, 1,2-benzanthraquinone, 1-methylanthraquinone, 2-ethylanthraquinone, 1-hydroxyanthraquinone, and the like.

Examples of the benzoin alkyl ether include benzoin methyl ether, benzoin ethyl ether, benzoin isopropyl ether, benzoin isobutyl ether, and the like.

Examples of the α-aminoketone include 2-methyl-1-[4-(methylthio)phenyl]-2-morpholinopropan-1-one, and the like.

The α-diketone is contained in an amount of preferably 50% by weight or more, more preferably 60% by weight or more, and even more preferably 65 to 100% by weight, of the photopolymerization initiator (c), from the viewpoint of photocuring property of the resulting cement for dental use.

In addition, the photopolymerization initiator other than the α-diketone is contained in an amount of preferably 50% by weight or less, more preferably 40% by weight or less, and even more preferably from 0 to 35% by weight, of the photopolymerization initiator (c), from the viewpoint of satisfying both photocuring property and aesthetic appreciation of the resulting cement for dental use.

The photopolymerization initiator (c) is blended in a total amount of 0.010 to 0.100 parts by weight, preferably from 0.010 to 0.095 parts by weight, more preferably from 0.010 to 0.090 parts by weight, even more preferably from 0.020 to 0.080 parts by weight, and even more preferably from 0.030 to 0.080 parts by weight, based on a total amount 100 parts by weight of the polymerizable monomer (a), from the viewpoint of excellent removability for an excess cement of the resulting cement for dental use. If the photopolymerization initiator (c) is blended in a total amount of 0.010 parts by weight or more, mechanical strength and bond strength of the cured product can be well maintained, and if the photopolymerization initiator (c) is blended in a total amount of 0.100 parts by weight or less, curing of an excess cement immediately after curing by photoirradiation becomes appropriate, so that removability of an excess cement would be excellent.

The cement for dental use of the present invention contains, in addition to the above-mentioned photopolymerization initiator (c), a chemical polymerization initiator (d). Since the cement contains the chemical polymerization initiator (d), not only a part to which light does not reach in a case where a photo-impermeable crowning restorative material is used can be polymerized, but also the polymerization initiation reaction takes place even after the removal of an excess cement, so that the polymerization and curing of the cement for dental use is accelerated, and that mechanical strength after removal of an excess cement can be increased. As the chemical polymerization initiator (d), a redox polymerization initiator composed of an oxidizing agent (f) and a reducing agent (g) is used, and the oxidizing agent (f) is contained in either one of the first agent and the second agent, and the reducing agent (g) is contained in the other.

The oxidizing agents (f) for the redox polymerization initiator are exemplified by organic peroxides, azo compounds, inorganic peroxides, and the like. The organic peroxides are exemplified by diacyl peroxides, peroxy esters, dialkyl peroxides, peroxyketals, ketone peroxides, and hydroperoxides. Specific examples of the diacyl peroxides include benzoyl peroxide, 2,4-dichlorobenzoyl peroxide, m-toluoyl peroxide, and the like. Specific examples of the peroxy esters include t-butyl peroxybenzoate, bis-t-butyl peroxyisophthalate, 2,5-dimethyl-2,5-bis(benzoylperoxy)hexane, t-butylperoxy-2-ethylhexanoate, t-butylperoxyisopropyl carbonate, and the like. Specific examples of the dialkyl peroxides include dicumyl peroxide, di-t-butyl peroxide, lauroyl peroxide, and the like. Specific examples of the peroxyketals include 1,1-bis(t-butylperoxy)3,3,5-trimethylcyclohexane, 1,1-bis(t-butylperoxy)cyclohexane, 1,1-bis(t-hexylperoxy)cyclohexane, and the like. Specific examples of the ketone peroxides include methyl ethyl ketone peroxide, cyclohexanone peroxide, methyl acetoacetate peroxide, and the like. Specific examples of the hydroperoxides include t-butyl hydroperoxide, cumene hydroperoxide, p-diisopropylbenzene peroxide, 1,1,3,3-tetramethylbutyl hydroperoxide, and the like. The azo compounds include azobisisobutyronitrile, azobisisobutylvaleronitrile, and the like. The inorganic peroxides include sodium persulfate, potassium persulfate, aluminum persulfate, ammonium persulfate, and the like.

The reducing agent (g) for the redox polymerization initiator includes aromatic amines without an electron withdrawing group in the aromatic ring, thioureas, ascorbic acid, and the like. Specific examples of the aromatic amines without an electron withdrawing group in the aromatic ring include N,N-bis(2-hydroxyethyl)-3,5-dimethylaniline, N,N-di(2-hydroxyethyl)-p-toluidine, N,N-bis(2-hydroxyethyl)-3, 4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, and the like. Any of the aromatic amines without having an electron withdrawing group in the aromatic ring mentioned above may be used alone, or in a combination of plural kinds. The thioureas include thiourea, methyl thiourea, ethyl thiourea, N,N'-dimethyl thiourea, N,N'-diethyl thiourea, N,N'-di-n-propyl thiourea, dicyclohexyl thiourea, trimethyl thiourea, triethyl thiourea, tri-n-propyl thiourea, tricyclohexyl thiourea, tetramethyl thiourea, tetraethyl thiourea, tetra-n-propyl thiourea, tetracyclohexyl thiourea, and the like. Any of the above-mentioned thiourea compounds may be added alone or in a combined use of plural kinds.

The chemical polymerization initiator (d) is blended in a total amount [a total amount of the above-mentioned oxidizing agent (f) and the above-mentioned reducing agent (g) blended] of from 0.001 to 20 parts by weight, based on 100 parts by weight of a total amount of the polymerizable monomer (a), from the viewpoint of curing property or the like of the resulting cement for dental use. As the amount of the chemical polymerization initiator (d) blended, if a total amount of the oxidizing agent and the reducing agent blended together is 0.001 parts by weight or more, mechanical strength and bond strength of the cured product can be satisfied, and the total amount is preferably 0.01 parts by weight or more, and more preferably 0.1 parts by weight or more. On the other hand, if the total amount of the chemical polymerization initiator (d) blended is 20 parts by weight or less, bond strength is not lowered, and the total amount is preferably 10 parts by weight or less, and more preferably 5 parts by weight or less. Therefore, the chemical polymerization initiator (d) is blended in a total amount of from 0.001 to 20 parts by weight, preferably from 0.01 to 10 parts by weight, and more preferably from 0.1 to 5, based on 100 parts by weight of a total amount of the polymerizable monomer (a).

In addition, a ratio of a total weight of the photopolymerization initiator (c) to a total weight of the chemical polymerization initiator (d) [photopolymerization initiator (c)/chemical polymerization initiator (d)] is preferably from 1/28 to 1/5, more preferably from 1/27 to 1/10, even more preferably from 1/27 to 1/12, and even more preferably from 1/25 to 1/20, from the viewpoint of controlling the initiation rate of radical polymerization by photopolymerization and chemical polymerization and controlling compression modulus immediately after photocuring and 24 hours thereafter, thereby satisfying both removability of an excess cement and mechanical strength.

In a preferred embodiment of the present invention, the photopolymerization initiator (c) and the chemical polymerization initiator (d) mentioned above are used together with the polymerization accelerator (e). The polymerization accelerator (e) usable in the present invention includes aliphatic amines, aromatic tertiary amines having an electron withdrawing group, sulfinic acid and salts thereof, sulfur-containing reducing inorganic compounds, borate compounds, barbituric acid derivatives, triazine compounds, copper compounds, tin compounds, vanadium compounds, halogenated compounds, aldehydes, thiol compounds and the like.

The aliphatic amines are exemplified by primary aliphatic amines such as n-butylamine, n-hexylamine, and n-octylamine; secondary aliphatic amines such as diisopropylamine, dibutylamine, and N-methyldiethanolamine; tertiary aliphatic amines such as N-methyldiethanolamine, N-ethyldiethanolamine, N-n-butyldiethanolamine, N-lauryldiethanolamine, 2-(dimethylamino)ethyl (meth)acrylate, N-methyldiethanolamine di(meth)acrylate, N-ethyldiethanolamine di(meth)acrylate, triethanolamine mono(meth)acrylate, triethanolamine di(meth)acrylate, triethanolamine tri(meth)acrylate, triethanolamine, trimethylamine, triethylamine, and tributylamine. Among them, the tertiary aliphatic amines are preferred, among which N-methyldiethanolamine and triethanolamine are preferred, from the viewpoint of curing property and storage stability of the composition.

The aromatic tertiary amines having an electron withdrawing group include compounds in which a hydrogen atom of the aromatic ring of the aromatic tertiary amines is replaced by an electron withdrawing group such as a carboxyl group, a carboxylic ester group, a nitrile group, or a halogen group. Specific examples include ethyl 4-N,N-dimethylaminobenzoate ester, methyl 4-N,N-dimethylaminobenzoate ester, propyl 4-N,N-dimethylaminobenzoate ester, n-butoxyethyl 4-N,N-dimethylaminobenzoate ester, 2-[(meth)acryloyloxy]ethyl 4-N,N-dimethylaminobenzoate ester, 4-N,N-dimethylaminobenzophenone, and the like. Among them, ethyl 4-N,N-dimethylaminobenzoate ester, methyl 4-N,N-dimethylaminobenzoate ester, n-butoxyethyl N,N-dimethylaminobenzoate ester, and 4-N,N-dimethylaminobenzophenone are preferred, from the viewpoint of curing property of the composition.

The sulfinic acids and salts thereof include, for example, p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, calcium 2,4,6-triisopropylbenzenesulfinate, and the like.

The sulfur-containing reducing inorganic compounds include sulfites, bisulfites, pyrosulfites, thiosulfates, thionates, hypothionates, and the like. Specific examples include sodium sulfite, potassium sulfite, calcium sulfite, ammonium sulfite, sodium hydrogensulfite, potassium hydrogensulfite, and the like.

The borate compounds are preferably aryl borate compounds. When preferably used aryl borate compounds are specifically exemplified, borate compounds having one aryl group in one molecule include trialkylphenyl borate, trialkyl (p-chlorophenyl) borate, trialkyl(p-fluorophenyl) borate, trialkyl(3,5-bistrifluoromethyl)phenyl borate, trialkyl[3,5-bis(1,1,1,3,3,3-hexafluoro-2-methoxy-2-propyl)phenyl]borate, trialkyl(p-nitrophenyl) borate, trialkyl(m-nitrophenyl) borate, trialkyl(p-butylphenyl) borate, trialkyl(m-butylphenyl) borate, trialkyl(p-butyloxyphenyl) borate, trialkyl(m-butyloxyphenyl) borate, trialkyl(p-octyloxyphenyl) borate, and trialkyl(m-octyloxyphenyl) borate (alkyl group being at least one member selected from the group consisting of an n-butyl group, an n-octyl group, and an n-dodecyl group, and the like) and salts thereof (sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, butylquinolinium salts, and the like).

In addition, the borate compounds having two aryl groups in one molecule include dialkyldiphenyl borate, dialkyldi(p-chlorophenyl) borate, dialkyldi(p-fluorophenyl) borate, dialkyldi(3,5-bistrifluoromethyl)phenyl borate, dialkyldi[3,5-bis(1,1,1,3,3,3-hexafluoro-2-methoxy-2-propyl)phenyl] borate, dialkyldi(p-nitrophenyl) borate, dialkyldi(m-nitrophenyl) borate, dialkyldi(p-butylphenyl) borate, dialkyldi(m-butylphenyl) borate, dialkyldi(p-butyloxyphenyl) borate, dialkyldi(m-butyloxyphenyl) borate, dialkyldi(p-octyloxyphenyl) borate, and dialkyldi(m-octyloxyphenyl) borate (alkyl group being at least one member selected from the group consisting of an n-butyl group, an n-octyl group, and an n-dodecyl group, and the like) and salts thereof (sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, butylquinolinium salts, and the like).

Further, the borate compounds having three aryl groups in one molecule include monoalkyltriphenyl borate, monoalkyltri(p-chlorophenyl) borate, monoalkyltri(p-fluorophenyl) borate, monoalkyltri(3,5-bistrifluoromethyl)phenyl borate, monoalkyltri[3,5-bis(1,1,1,3,3,3-hexafluoro-2-methoxy-2-propyl)phenyl]borate, monoalkyltri(p-nitrophenyl) borate, monoalkyltri(m-nitrophenyl) borate, monoalkyltri(p-butylphenyl) borate, monoalkyltri(m-butylphenyl) borate, monoalkyltri(p-butyloxyphenyl) borate, monoalkyltri(m-butyloxyphenyl) borate, monoalkyltri(p-octyloxyphenyl) borate, and monoalkyltri(m-octyloxyphenyl) borate (alkyl group being at least one member selected from the group consisting of an n-butyl group, an n-octyl group, and an n-dodecyl group, and the like) and salts thereof (sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, butylquinolinium salts, and the like).

Further, the borate compounds having four aryl groups in one molecule include tetraphenyl borate, tetrakis(p-chlorophenyl) borate, tetrakis(p-fluorophenyl) borate, tetrakis(3,5-bistrifluoromethyl)phenyl borate, tetrakis[3,5-bis(1,1,1,3,3,3-hexafluoro-2-methoxy-2-propyl)phenyl]borate, tetrakis(p-nitrophenyl) borate, tetrakis(m-nitrophenyl) borate, tetrakis(p-butylphenyl) borate, tetrakis(m-butylphenyl) borate, tetrakis(p-butyloxyphenyl) borate, tetrakis(m-butyloxyphenyl) borate, tetrakis(p-octyloxyphenyl) borate, tetrakis(m-octyloxyphenyl) borate, (p-fluorophenyl)triphenyl borate, (3,5-bistrifluoromethyl)phenyltriphenyl borate, (p-nitrophenyl)triphenyl borate, (m-butyloxyphenyl)triphenyl borate, (p-butyloxyphenyl)triphenyl borate, (m-octyloxyphenyl)triphenyl borate, and (p-octyloxyphenyl)triphenyl borate, and salts thereof (sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, butylquinolinium salts, and the like).

The barbituric acid derivatives include barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid and thiobarbituric acids, and salts thereof (preferably an alkali metal or alkaline earth metal), and salts of these barbituric acids include, for example, sodium 5-butylbarbiturate, sodium 1,3,5-trimethylbarbiturate and sodium 1-cyclohexyl-5-ethylbarbiturate, and the like.

Triazine compounds include, for example, 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-($\alpha,\alpha,\beta$-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino]ethoxy}-4,6-bis(trichloromethyl)-s-triazine, 2-[2-{N-hydroxyethyl-N-methylamino}ethoxy]-4,6-bis(trichloromethyl)-s-triazine, 2-[2-{N,N-diallylamino}ethoxy]-4,6-bis(trichloromethyl)-s-triazine, and the like.

As the copper compounds, for example, copper acetyl acetone, cupric acetate, copper oleate, cupric chloride, cupric bromide, or the like is suitably used.

The tin compounds include, for example, di-n-butyltin dimalate, di-n-octyltin dimalate, di-n-octyltin dilaurate, di-n-butyltin dilaurate, and the like. Among them, the preferred tin compounds are di-n-octyltin dilaurate and di-n-butyltin dilaurate.

The vanadium compounds are preferably vanadium compounds of the oxidation state of IV and/or V. The vanadium compounds of the oxidation state of IV and/or V include, for example, those compounds listed in Japanese Patent Laid-Open No. 2003-96122, such as vanadium (IV) tetroxide, vanadium (IV) oxide acetyl acetonate, vanadyl (IV) oxalate, vanadyl (IV) sulfate, oxobis(1-phenyl-1,3-butanedionate) vanadium (IV), bis(maltolate)oxovanadium (IV), vanadium (V) pentoxide, sodium metavanadate (V), and ammonium metavanadate (V).

As the halogenated compound, for example, dilauryldimethylammonium chloride, lauryldimethylbenzylammonium chloride, benzyltrimethylammonium chloride, tetramethylammonium chloride, benzyldimethylcetylammonium chloride, dilauryldimethylammonium bromide, or the like is suitably used.

The aldehyde includes, for example, terephthalic aldehyde, benzaldehyde derivatives, and the like. The benzaldehyde derivative includes dimethylaminobenzaldehyde, p-methyloxybenzaldehyde, p-ethyloxybenzaldehyde, p-n-octyloxybenzaldehyde, and the like.

The thiol compound includes, for example, 3-mercaptopropyltrimethoxysilane, 2-mercaptobenzooxazole, decanethiol, thiobenzoic acid, and the like.

Among the above-mentioned polymerization accelerators (e), the aromatic tertiary amines having an electron withdrawing group, the sulfinic acids and salts thereof, the sulfur-containing reducing inorganic compounds are preferred, and at least one member selected from the group consisting of ethyl 4-N,N-dimethylaminobenzoate ester, methyl 4-N,N-dimethylaminobenzoate ester, n-butoxyethyl N,N-dimethylaminobenzoate ester, 4-N,N-dimethylaminobenzophenone, sodium benzenesulfinate, sodium p-toluenesulfinate, sodium 2,4,6-triisopropylbenzenesulfinate, sodium sulfite, potassium sulfite, calcium sulfite, ammonium sulfite, sodium hydrogensulfite, and potassium hydrogensulfite is more preferred, from the viewpoint of having a large increase in mechanical strength after removal of an excess cement.

The amount of the polymerization accelerator (e) blended is not particularly limited, and it is preferable that the polymerization accelerator (e) is contained in an amount of from 0.001 to 20 parts by weight, based on a total amount 100 parts by weight of the polymerizable monomer (a), from the curing property or the like of the resulting composition. If the polymerization accelerator (e) is blended in an amount of 0.001 parts by weight or more, mechanical strength and bond strength of the cured product become favorable, and the polymerization accelerator is blended in an amount of more preferably 0.01 parts by weight or more, and even more preferably 0.1 parts by weight or more. On the other hand, if the polymerization accelerator (e) is blended in an amount of 20 parts by weight or less, the color tone of the composition does not worsen without lowering bond strength, so that discoloration of the cured product can be prevented, and the polymerization accelerator is blended in an amount of more preferably 15 parts by weight or less, even more preferably 10 parts by weight or less, and even more preferably 5 parts by weight or less.

The cement for dental use of the present invention can be blended with a known additive within the range so as not to lower the performance. The additive includes polymerization inhibitors, antioxidants, pigments, dyes, ultraviolet absorbents, organic solvents, thickening agents, or the like.

The cement for dental use of the present invention is not particularly limited, so long as the cement for dental use contains the polymerizable monomer (a), the filler (b), the photopolymerization initiator (c) and the chemical polymerization initiator (d), and the cement for dental use can be easily produced by a method known to one of ordinary skill in the art as a resin cement or a resin-modified glass ionomer cement.

In addition, since the chemical polymerization initiator (d) is a redox polymerization initiator composed of an oxidizing agent (f) and a reducing agent (g), each of the oxidizing agent (f) and the reducing agent (g) mentioned above is stored in separate containers, from the viewpoint of storage stability. In other words, in an embodiment, the cement for dental use of the present invention is provided as a kit used in a two-agent form, and in a preferred embodiment, the cement for dental use is provided as a kit used in the form of two paste forms. When the cement is used in the 2-paste form, it is preferable that each of the pastes is stored in the state where the pastes are separated from each other, and the two pastes are mixed immediately before use, so that the chemical polymerization and the photopolymerization are progressed and cured.

When the cement for dental use of the present invention is used as a resin cement, it is preferable that the cement for dental use is a composition containing (a), (b), (c), (d) and (e). In a case where the cement for dental use is in the form of 2-paste manufactured article, when the above-mentioned two pastes are referred to A paste and B paste, respectively, it is preferable that both the A and B pastes contain the above-mentioned polymerizable monomer (a) and the above-mentioned filler (b), that at least one of the pastes contains the above-mentioned photopolymerization initiator (c), and further that either one of the pastes contains an oxidizing agent (f) and the other contains a reducing agent (g) for the above-mentioned chemical polymerization initiator (d), respectively, and that either one of the pastes contains a polymerization accelerator (e). Here, in a case where the polymerizable monomer (a) contains a polymerizable monomer containing an acidic group, it is preferable that the polymerizable monomer containing an acidic group is contained in either one of the A and B pastes.

In addition, in a case where the cement for dental use of the present invention is used as a resin-modified glass ionomer cement, the cement for dental use contains typically an inorganic filler such as fluoroaluminosilicate glass, a polyalkenic acid such as polyacrylic acid, and water, and it is desired that the cement for dental use has a composition in a manner that these components have a mechanism of reaction and curing by an acid-base reaction, and specifically, it is preferable that the cement is a composition containing (a), (b), (c), (d), (e), polyalkenic acid, and water. Here, in the mechanism, it is considered that an adhesive function is exhibited by an interaction of the above-mentioned polyalkenic acid and calcium in hydroxyapatite constituting the dentine.

The polyalkenic acid refers to a polymer of an unsaturated monocarboxylic acid or an unsaturated dicarboxylic acid. Specific examples of the above-mentioned polyalkenic acid include homopolymers of acrylic acid, methacrylic acid, 2-chloroacrylic acid, 2-cyanoacrylic acid, aconitic acid, mesaconic acid, maleic acid, itaconic acid, fumaric acid, glutaconic acid, citraconic acid, utraconic acid, or copolymers of these unsaturated carboxylic acids and copolymerizable monomers. In the case of the copolymer, it is preferable that the proportion of the unsaturated carboxylic acid units is 50% by mol or more of the entire structural units. The copolymerizable monomer is preferably an ethylenically unsaturated polymerizable monomer, and the copolymerizable monomer includes, for example, styrene, acrylamide, acrylonitrile, methyl methacrylate, salts of acrylic acid, vinyl chloride, allyl chloride, vinyl acetate, 1,1,6-trimethylhexamethylene dimethacrylate ester, and the like. Among these polyalkenic acid, the homopolymers or copolymers of acrylic acid or maleic acid are preferred. When these polyalkenic acids have a weight-average molecular weight of less than 5,000, strength of the cured product of the cement composition for dental use is lowered, so that its durability is worsened in some cases. On the other hand, when these polyalkenic acids have a weight-average molecular weight exceeding a viscosity of 40,000, upon mixing and blending the cement composition for dental use becomes harder, so that operability is lowered in some cases. Therefore, the preferred weight-average molecular weight of the polyalkenic acid is from 5,000 to 40,000. These polyalkenic acids are blended in an amount so that they are contained in an amount of preferably from 1 to 200 parts by weight, more preferably from 5 to 100 parts by weight, and even more preferably from 10 to 50 parts by weight, based on 100 parts by weight of a total amount of the polymerizable monomer (a). Since the polyalkenic acid is contained in the range defined above, curing caused by an acid-base reaction smoothly progresses, and the disintegration by hydrolysis or the like in the oral cavity of the resulting cured product can be made smaller.

As the filler (b) usable in a case where the cement for dental use of the present invention is used as a resin-modified glass ionomer cement, among the above-mentioned inorganic fillers, it is preferable to use at least one member selected from the group consisting of fluoroaluminosilicate glass, calcium fluoroaluminosilicate glass, strontium fluoroaluminosilicate glass, barium fluoroaluminosilicate glass, and strontium calcium fluoroaluminosilicate glass, and it is more preferable to use fluoroaluminosilicate glass and/or barium fluoroaluminosilicate glass, from the viewpoint of curing property in the acid-base reaction and fluorine sustained releasability of the composition.

In addition, the water usable in a case where the cement for dental use of the present invention is used as a resin-modified glass ionomer cement is blended in an amount so that the cement for dental use contains water in an amount of preferably from 5 to 500 parts by weight, more preferably from 10 to 300 parts by weight, and even more preferably from 20 to 100 parts by weight, based on 100 parts by weight of a total amount of the polymerizable monomer (a). Since the water is contained in the range defined above, an acid-base reaction can be smoothly progressed, and mechanical strength of the resulting cured product and adhesion to the dentine become excellent.

As mentioned above, since curing takes place due to the progress of the acid-base reaction in the resin-modified glass ionomer cement, it is preferable that the filler (b) and the polyalkenic acid are packaged in separate containers, and blended immediately before use to be used, from the viewpoint of storage stability. In the case of the 2-paste form manufacturing article, when the two pastes are referred to as A paste and B paste, respectively, it is preferable that the above-mentioned A paste contains the above-mentioned polymerizable monomer (a), the above-mentioned filler (b), the polyalkenic acid and water, and that the above-mentioned B paste contains the above-mentioned polymerizable monomer (a) and the above-mentioned filler (b), and that at least one of the pastes contains the above-mentioned photopolymerization initiator (c), and that further either one of the pastes contains the oxidizing agent (f), and the other contains the reducing agent (g) for the above-mentioned chemical polymerization initiator (d), and that either one of the pastes contains the polymerization accelerator (e), respectively. Also, it is preferable that the above-mentioned A paste contains the above-mentioned polymerizable monomer (a), the above-mentioned filler (b) and the polyalkenic acid, and that the above-mentioned B paste contains the above-mentioned polymerizable monomer (a), the above-mentioned filler (b), and water, and that at least one of the pastes contains the above-mentioned photopolymerization initiator (c), and further that either one of the pastes contains the oxidizing agent (f), and the other contains the reducing agent (g) for the above-mentioned chemical polymerization initiator (d), and that either one of the pastes contains the polymerization accelerator (e), respectively. In any of the embodiments, since the polyalkenic acid is contained on the side of the above-mentioned A paste, as the filler (b) contained in the above-mentioned B paste, it is preferable to use at least one member selected from the group consisting of fluoroaluminosilicate glass, calcium fluoroaluminosilicate glass, strontium fluoroaluminosilicate glass, barium fluoroaluminosilicate glass, and strontium calcium fluoroaluminosilicate glass, and it is more preferable to use the fluoroaluminosilicate glass and/or the barium fluoroaluminosilicate glass. On the other hand, as the filler (b) contained in the above-mentioned A paste, it is preferable to use those not showing reactivity to the polyalkenic acid, and quartz is preferably used.

The cement for dental use of the present invention thus obtained has a compression modulus of the cured product immediately after photo-curing of from 100 to 400 MPa. The compression modulus refers to an index showing hardness, that is a value indicating how much force is needed to be applied per unit area, to compress a certain substance to make its thickness zero. The larger this value, the harder the substance, and the cement for dental use has a compression modulus immediate after photoirradiation of from 100 to 400 MPa, preferably from 150 to 370 MPa, more preferably from 200 to 350 MPa, and even more preferably from 250 to 350 MPa, from the viewpoint of removability of an excess cement. If the cement for dental use has a compression modulus immediately after photoirradiation of 100 MPa or more, the mechanical strength to an extent that can remove an excess cement after curing in a single lump is obtained, thereby showing excellent removability. On the other hand, if the cement for dental use has a compression modulus immediately after photoirradiation of 400 MPa or less, mechanical strength of the cement for dental use immediately after photoirradiation does not become too high, so that the removal of an excess cement is facilitated without firmly adhering to the dentine or the dental restorative material. The compression modulus for the cement for dental use as used herein is measured in accordance with the method described in Examples described below.

In addition, the cement for dental use of the present invention has a compression modulus after 24 hours from photoirradiation of 500 MPa or more. The cement for dental use has a compression modulus after 24 hours from the photoirradiation is preferably from 600 to 1500 MPa, more preferably from 750 to 1500 MPa, and even more preferably from 900 to 1500 MPa, from the viewpoint of maintaining durability against a pressure such as an engaging pressure. In a case where the cement for dental use has a compression modulus after 24 hours from photoirradiation of 500 MPa or more, a strain against a pressure such as an engaging pressure does not become too large, so that there is no risks that the cement for dental use is disintegrated, or that the dental restorative material is detached even when applied to the oral cavity for a long period of time.

Subsequently, a method of use upon adhering the dentine and a crowning restorative material using the cement for dental use of the present invention will be explained by taking a manufactured article in the two-paste form as an example. The A paste and the B paste for the cement for dental use of the present invention are blended immediately before use to form one paste, and thereafter the cement for dental use in slight excess amount before the beginning of curing is applied to an inner wall side of the crowning restorative material and pressed against the dentine. During the pressing operation, an excess part of the cement for dental use is allowed to run off the bonding part (marginal part) of the dentine and the crowning restorative material, and the run-off excess cement is subjected to provisional irradiation using a photoirradiator for dental use to form an excess cement into a semi-cured state. The photoirradiation time for making the semi-cured state differs depending upon the kinds and the amount of light of the photoirradiator, and is usually from 2 to 5 seconds or so. Thus, the excess cement is removed using a dental probe or the like for the excess cement in a semi-cured state. Before the application of the cement for dental use of the present invention to dentine surface, the dentine surface may be subjected to a conventionally known pretreatment such as an etching treatment with an aqueous acidic solution, a modification treatment with a primer, an etching-modification concurrent treatment with a primer having an etching ability, or the like. Known ones can be used as these surface treatment agents without limitation.

EXAMPLES

The present invention will be specifically described hereinbelow on the bases of Examples and Comparative Examples, without intending to limit the scope of the present invention to these Examples and the like.

Here, the abbreviations used hereinafter are as follows.
[Polymerizable Monomer (a)]
D-2.6E: 2,2-Bis(4-methacryloyloxypolyethoxyphenyl)propane
NPG: Neopentyl glycol di(meth)acrylate
Bis-GMA: 2,2-Bis [4-(3-methacryloyoxy)-2-hydroxypropoxyphenyl]propane
MDP: 10-Methacryloyloxydecyl dihydrogenphosphate
[Filler (b)]

The inorganic fillers 1 and 2 are obtained in accordance with the following production methods.

Inorganic Filler 1: Silane-treated barium glass powder

Barium glass (manufactured by Estec Corp., under the market product code "Raysorb E-3000") was pulverized with a ball-mill, to give a barium glass powder. The average particle size of the resulting barium glass powder was measured using a laser diffraction particle size distribution analyzer (manufactured by Shimadzu Corporation, model "SALD-2100"). As a result, the average particle size was 2.4 μm. This barium glass particle powder was surface-treated with 3 parts by weight of 3-methacryloyloxypropyl trimethoxysilane, based on 100 parts by weight of the barium glass powder, to give a silane-treated barium glass powder.

Inorganic Filler 2: Silane-treated colloidal silica powder

In 100 parts by weight of distilled water were added 0.3 parts by weight of acetic acid and 3 parts by weight of 3-methacryloyloxypropyl trimethoxysilane while stirring, and further 50 parts by weight of a colloidal silica powder (manufactured by Nippon Aerosil Co., Ltd., market product code "Aerosil OX50") were added thereto, and the mixture was stirred for 1 hour. Water was removed from the mixture by lyophilization, and thereafter the product was heat-treated at 80° C. for 5 hours, to give a silane-treated colloidal silica powder.

[Photopolymerization Initiator (c)]
CQ: dl-Camphorquinone
2,4,6-Trimethylbenzoyl diphenyl phosphine oxide
[Chemical Polymerization Initiator (d): Oxidizing Agent (f)]
BPO: Benzoyl peroxide
[Chemical Polymerization Initiator (d): Reducing Agent (g)]
DEPT: N,N-Di(2-hydroxyethyl)-p-toluidine
[Polymerization Accelerator (e)]
DBB: n-Butoxyethyl N,N-dimethylaminobenzoate ester
TPBSS: Sodium 2,4,6-triisopropylbenzenesulfinate
[Polymerization Inhibitor]
BHT: 2,6-Di-t-butyl-4-methylphenol Examples 1 to 12 and Comparative Examples 1 to 3

Preparation of Dual Curing Resin Cement

The raw materials shown in Table 1 or 2 were mixed at an ambient temperature to prepare A paste and B paste, and the properties were evaluated in accordance with the following methods of Test Examples 1 to 3. The results are shown in Tables 1 and 2.

Test Example 1

Compression Modulus Immediately After Photoirradiation

For each of Examples and Comparative Examples, A paste and B paste measured in an equal volume were mixed with a mixing spatula for dental use for 10 seconds, and thereafter the mixture was immediately charged in a mold made of stainless steel having a hole of a diameter of 4 mm and a height of 4 mm. The top and bottom sides of the mold are pressed with a releasing film (polyester), and after 1 minute from the beginning of mixing, the cement for dental use was photoirradiated with an irradiating device "JET Light 3000" (manufactured by J. Morita USA) from an upper side for 20 seconds, via the above-mentioned releasing film. Subsequently, the mold made of stainless steel was placed up-side-down, the side opposite thereto was also photoirradiated for 20 seconds, and thereafter, and the cured product was taken out of the mold to give one cured product of the cement for dental use. Further, in the same manner, three cured products were prepared, to give a total of four cured products of the cement for dental use.

After 3 minutes from the beginning of blending the cement for dental use, one of the cured product of the resulting cement for dental use was compressed using a compression tester (Autograph, manufactured by Shimadzu Corporation) at a crosshead speed of 1 mm/min, and the compression modulus of the cured product was measured at a test force of between 50N and 100N according to least square method. In the same manner, the compression moduli of the remaining three cured products were measured after 3 minutes from the beginning of mixing of the cement for dental use, and an average of the four compression moduli is defined as a value for the compression modulus immediately after the photoirradiation.

Test Example 2

Compression Modulus After 24 Hours

A cured product for the cement for dental use was prepared in the same manner as in Test Example 1, the resulting cured product was immersed in water at 37° C. for 24 hours, and thereafter the compression modulus was measured in the same manner as in Test Example 1. The compression moduli of the remaining three cured products were measured, and an average of the four compression moduli is defined as a value for compression modulus after 24 hour.

Test Example 3

Removability of Excess Cement

The labial side of the mandibular incisor of the bovine teeth was grinded with silicon carbide paper under running water to expose a flat surface of the dentine. The exposed flat surface was further grinded with a #1000 silicon carbide paper under running water, and water on the surface was air-blown to dry the surface. Thereafter, for each of Examples and Comparative Examples, 0.5 g of the cement for dental use of each of Examples and Comparative Examples, obtained by mixing the A paste and the B paste taken in equal volumes for 10 seconds, was applied to the smooth surface after drying, and a 5 mm×5 mm stainless steel plate was pressed from the top. An excess cement pushed out by pressing was subjected to photoirradiation for 5 seconds each from each of the four sides of the stainless plate using the irradiation device for dental use "JET Light 3000" in the same manner as in Test Example 1. Thereafter, an excess resin was removed with a probe, and removability of an excess cement was evaluated in accordance with the following evaluation criteria.

(Evaluation Criteria for Removability of Excess Cement)

A: being capable of removing an excess cement easily in a single lump;

B: an excess cement being hard and adhered to the dentine, but being capable of removing in a single lump;

C: an excess cement being brittle, but being capable of removing only the excess cement;

D: an excess cement being brittle, thereby causing excess removal from the pressing part; and E: an excess cement having a high strength and being firmly adhered to the dentine, thereby making it difficult to remove

TABLE 1

|  | Example 1 | | Example 2 | | Example 3 | | Example 4 | |
| --- | --- | --- | --- | --- | --- | --- | --- | --- |
|  | A | B | A | B | A | B | A | B |
| Raw Materials | | | | | | | | |
| D-2.6E(a) | 20 | 30 | 20 | 30 | 20 | 30 | 20 | 30 |
| NPG(a) | 10 | 20 | 10 | 20 | 10 | 20 | 10 | 20 |
| Bis-GMA(a) | 10 | — | 10 | — | 10 | — | 10 | — |
| MDP(a) | 10 | — | 10 | — | 10 | — | 10 | — |
| Inorganic Filler 1 (b) | 70 | 70 | 70 | 70 | 70 | 70 | 70 | 70 |
| Inorganic Filler 2 (b) | 22.5 | 22.5 | 22.5 | 22.5 | 22.5 | 22.5 | 22.5 | 22.5 |
| CQ (c) | 0.050 | — | 0.050 | — | 0.050 | — | 0.050 | — |
| TMDPO (c) | — | — | — | — | — | — | — | — |
| BPO(d: Oxidizing Agent (f)) | 1.0 | — | 1.0 | — | 1.0 | — | 1.0 | — |
| DEPT(d: Reducing Agent (g)) | — | 0.2 | — | 0.2 | — | 0.2 | — | 0.2 |
| DBB (e) | — | 0.15 | — | 0.15 | — | 0.15 | — | 0.15 |
| TPBSS (e) | — | — | — | 0.25 | — | 0.5 | — | 1.0 |
| Sodium Sulfite[1] (e) | — | — | — | — | — | — | — | — |
| BHT | 0.025 | 0.025 | 0.025 | 0.025 | 0.025 | 0.025 | 0.025 | 0.025 |
| (c)/(d)[2] | 1/24 | | 1/24 | | 1/24 | | 1/24 | |
| Properties | | | | | | | | |
| Compression Modulus (Immediately After) (MPa) | 277 | | 293 | | 318 | | 332 | |
| Compression Modulus (24 h) (MPa) | 788 | | 968 | | 1030 | | 1047 | |
| Removability of Excess Cement | A | | A | | A | | A | |

|  | Example 5 | | Example 6 | | Example 7 | | Example 8 | |
| --- | --- | --- | --- | --- | --- | --- | --- | --- |
|  | A | B | A | B | A | B | A | B |
| Raw Materials | | | | | | | | |
| D-2.6E(a) | 20 | 30 | 20 | 30 | 20 | 30 | 20 | 30 |
| NPG(a) | 10 | 20 | 10 | 20 | 10 | 20 | 10 | 20 |
| Bis-GMA(a) | 10 | — | 10 | — | 10 | — | 10 | — |
| MDP(a) | 10 | — | 10 | — | 10 | — | 10 | — |
| Inorganic Filler 1 (b) | 70 | 70 | 70 | 70 | 70 | 70 | 70 | 70 |
| Inorganic Filler 2 (b) | 22.5 | 22.5 | 22.5 | 22.5 | 22.5 | 22.5 | 22.5 | 22.5 |
| CQ (c) | 0.050 | — | 0.050 | — | 0.050 | — | 0.050 | — |
| TMDPO (c) | — | — | — | — | — | — | — | — |
| BPO(d: Oxidizing Agent (f)) | 1.0 | — | 0.5 | — | 2.0 | — | 3.0 | — |
| DEPT(d: Reducing Agent (g)) | — | 0.2 | — | 0.2 | — | 0.2 | — | 0.2 |
| DBB (e) | — | 0.15 | — | 0.15 | — | 0.15 | — | 0.15 |
| TPBSS (e) | — | — | — | 0.25 | — | 0.25 | — | 0.25 |
| Sodium Sulfite[1] (e) | — | 1 | — | — | — | — | — | — |
| BHT | 0.025 | 0.025 | 0.025 | 0.025 | 0.025 | 0.025 | 0.025 | 0.025 |
| (c)/(d)[2] | 1/24 | | 1/14 | | 1/44 | | 1/64 | |
| Properties | | | | | | | | |
| Compression Modulus (Immediately After) (MPa) | 305 | | 263 | | 359 | | 381 | |
| Compression Modulus (24 h) (MPa) | 1055 | | 728 | | 953 | | 1003 | |
| Removability of Excess Cement | A | | A | | B | | B | |

*The amount of the raw materials used is expressed as parts by weight based on 100 parts by weight of a total amount of the polymerizable monomer contained in the entire resin cement.
[1]Fine sodium sulfite powder of the lyophilized product
[2]Ratio of a total weight of the photopolymerization initiator to a total weight of the chemical polymerization initiator (photopolymerization initiator/chemical polymerization initiator)

TABLE 2

|  | Example 9 | | Example 10 | | Example 11 | | Example 12 | |
| --- | --- | --- | --- | --- | --- | --- | --- | --- |
|  | A | B | A | B | A | B | A | B |
| Raw Materials | | | | | | | | |
| D-2.6E(a) | 20 | 30 | 20 | 30 | 20 | 30 | 20 | 30 |
| NPG(a) | 10 | 20 | 10 | 20 | 10 | 20 | 10 | 20 |
| Bis-GMA(a) | 10 | — | 10 | — | 10 | — | 10 | — |
| MDP(a) | 10 | — | 10 | — | 10 | — | 10 | — |
| Inorganic Filler 1 (b) | 70 | 70 | 70 | 70 | 70 | 70 | 70 | 70 |
| Inorganic Filler 2 (b) | 22.5 | 22.5 | 22.5 | 22.5 | 22.5 | 22.5 | 22.5 | 22.5 |
| CQ (c) | 0.025 | — | 0.075 | — | 0.095 | — | 0.050 | — |
| TMDPO (c) | — | — | — | — | — | — | 0.010 | — |
| BPO (d: Oxidizing Agent (f)) | 1.0 | — | 1.0 | — | 1.0 | — | 1.0 | — |
| DEPT (d: Reducing Agent (g)) | — | 0.2 | — | 0.2 | — | 0.2 | — | 0.2 |
| DBB (e) | — | 0.15 | — | 0.15 | — | 0.15 | — | 0.15 |
| TPBSS (e) | — | — | — | — | — | — | — | 0.25 |
| Sodium Sulfite[1] (e) | — | — | — | — | — | — | — | — |
| BHT | 0.025 | 0.025 | 0.025 | 0.025 | 0.025 | 0.025 | 0.025 | 0.025 |
| (c)/(d)[2] | 1/48 | | 1/16 | | 1/12.6 | | 1/20 | |
| Properties | | | | | | | | |
| Compression Modulus (Immediately After) (MPa) | 115 | | 327 | | 391 | | 315 | |
| Compression Modulus (24 h) (MPa) | 719 | | 814 | | 885 | | 991 | |
| Removability of Excess Cement | C | | A | | B | | A | |

|  | Comparative Example 1 | | Comparative Example 2 | | Comparative Example 3 | |
| --- | --- | --- | --- | --- | --- | --- |
|  | A | B | A | B | A | B |
| Raw Materials | | | | | | |
| D-2.6E(a) | 20 | 30 | 20 | 30 | 20 | 30 |
| NPG(a) | 10 | 20 | 10 | 20 | 10 | 20 |
| Bis-GMA(a) | 10 | — | 10 | — | 10 | — |
| MDP(a) | 10 | — | 10 | — | 10 | — |
| Inorganic Filler 1 (b) | 70 | 70 | 70 | 70 | 70 | 70 |
| Inorganic Filler 2 (b) | 22.5 | 22.5 | 22.5 | 22.5 | 22.5 | 22.5 |
| CQ (c) | 0.005 | — | 0.125 | — | 0.110 | — |
| TMDPO (c) | — | — | — | — | — | — |
| BPO (d: Oxidizing Agent (f)) | 1.0 | — | 1.0 | — | 2.75 | — |
| DEPT (d: Reducing Agent (g)) | — | 0.2 | — | 0.2 | — | 0.55 |
| DBB (e) | — | 0.15 | — | 0.15 | — | 0.15 |
| TPBSS (e) | — | — | — | — | — | — |
| Sodium Sulfite[1] (e) | — | — | — | — | — | — |
| BHT | 0.025 | 0.025 | 0.025 | 0.025 | 0.025 | 0.025 |
| (c)/(d)[2] | 1/240 | | 1/9.6 | | 1/30 | |
| Properties | | | | | | |
| Compression Modulus (Immediately After) (MPa) | 70 | | 435 | | 472 | |
| Compression Modulus (24 h) (MPa) | 108 | | 936 | | 995 | |
| Removability of Excess Cement | D | | E | | E | |

*The amount of the raw materials used is expressed as parts by weight based on 100 parts by weight of a total amount of the polymerizable monomer contained in the entire resin cement.
[1] Fine sodium sulfite powder of the lyophilized product
[2] Ratio of a total weight of the photopolymerization initiator to a total weight of the chemical polymerization initiator (photopolymerization initiator/chemical polymerization initiator)

It can be seen from the above that the resin cements of Examples satisfy both mechanical strength and removability of an excess cement, as compared to the resin cements of Comparative Examples. Among them, in a case of Example 9 where while the amount of the chemical polymerization initiator (d) contained is the same as that of Example 1, the amount of the photopolymerization initiator (c) contained is 0.025 parts by weight, based on 100 parts by weight of a total amount of the polymerizable monomer (a), or a case of Example 8 where while the amount of the photopolymerization initiator (c) contained is the same as that of Example 1, the amount of the chemical polymerization initiator (d) contained is 3.2 parts by weight, based on 100 parts by weight of a total amount of the polymerizable monomer (a), appropriate levels of mechanical strength and removability of an excess cement are maintained, while being slightly poorer in removability of the excess cement. In addition, in cases of Examples 1 to 5 and Example 10 where a ratio of a total weight of the photopolymerization initiator to a total weight of the chemical polymerization initiator is within a specified range, and a total amount of the photopolymerization initiator formulated is within a specified range, removability of an excess cement and an appropriate level of mechanical strength are further satisfied in a higher order, suggesting that it is important that each of the amounts of the photopolymerization initiator (c) and the chemical polymerization initiator (d) contained is within a specified range. In addition, it can be seen from Examples 2 to 5 that compression modulus after 24 hours is increased by using sodium 2,4,6-triisopropylbenzenesulfinate (TPBSS), or sodium sulfite as the polymerization accelerator (e).

INDUSTRIAL APPLICABILITY

The cement for dental use of the present invention is suitably used for adhering the dentine and a crowning restorative material in the field of dental therapy, or the like.

The invention claimed is:

1. A cement, comprising:
   (A) a first agent comprising
      (a1) a first polymerizable monomer,
      (b1) a first filler,
      (c) optionally, a photopolymerization initiator comprising an α-diketone, and
      (d) an oxidizing agent; and
   (B) a second agent comprising
      (a2) a second polymerizable monomer, which is the same or different from (a1),
      (b2) a second filler, which is the same or different from (b1),
      (c) optionally, the photopolymerization initiator, and
      (e) a reducing agent,
   wherein:
      the photopolymerization initiator (c) is present in at least one of the first agent and the second agent, and a total amount of the photopolymerization initiator (c) is from 0.010 to 0.100 parts by weight, based on 100 parts by weight of a total amount of the polymerizable monomers (a1) and (a2);
      the oxidizing agent (d) and the reducing agent (e) together form a redox polymerization initiator, and a total amount of the oxidizing agent (d) and the reducing agent (e) is from 0.001 to 20 parts by weight, based on 100 parts by weight of the total amount of the polymerizable monomers (a1) and (a2);
      a ratio of a total weight of the photopolymerization initiator (c) to a total weight of the oxidizing agent (d) and the reducing agent (e), (c)/((d)+(e)), is from 1/27 to 1/10; and
      a cured product of the cement has a first compression modulus immediately after photocuring the cement in a range from 100 to 400 MPa, and a second compression modulus 24 hours after the photocuring of 500 MPa or more.

2. The cement of claim 1, wherein the polymerizable monomers (a1) and (a2) each independently comprise at least one polymerizable group selected from the group consisting of a (meth)acryl group and a (meth)acrylamide group.

3. The cement of claim 1, further comprising:
   a polymerization accelerator (f) in an amount from 0.001 to 20 parts by weight, based on 100 parts by weight of a total amount of the polymerizable monomers (a1) and (a2).

4. The cement of claim 3, wherein the polymerization accelerator (f) is at least one selected from the group consisting of ethyl 4-N,N-dimethylaminobenzoate ester, methyl 4-N,N-dimethylaminobenzoate ester, n-butoxyethyl N,N-dimethylaminobenzoate ester, 4-N,N-dimethylaminobenzophenone, sodium benzenesulfinate, sodium p-toluenesulfinate, sodium 2,4,6-triisopropylbenzenesulfinate, sodium sulfite, potassium sulfite, calcium sulfite, ammonium sulfite, sodium hydrogensulfite, and potassium hydrogensulfite.

5. The cement of claim 1, wherein the first agent is a first paste (A), and the second agent is a second paste (B).

6. The cement of claim 2, further comprising:
   a polymerization accelerator (f) in an amount of from 0.001 to 20 parts by weight, based on 100 parts by weight of a total amount of the polymerizable monomers (a1) and (a2).

7. The cement of claim 6, wherein the polymerization accelerator (f) is at least one selected from the group consisting of ethyl 4-N,N-dimethylaminobenzoate ester, methyl 4-N,N-dimethylaminobenzoate ester, n-butoxyethyl N,N-dimethylaminobenzoate ester, 4-N,N-dimethylaminobenzophenone, sodium benzenesulfinate, sodium p-toluenesulfinate, sodium 2,4,6-triisopropylbenzenesulfinate, sodium sulfite, potassium sulfite, calcium sulfite, ammonium sulfite, sodium hydrogensulfite, and potassium hydrogensulfite.

8. The cement of claim 2, wherein the first agent is a first paste (A), and the second agent is a second paste (B).

9. The cement of claim 1, wherein a total content of the photopolymerization initiator (c) is from 0.010 to 0.095 parts by weight, based on 100 parts by weight of the total amount of the polymerizable monomers (a1) and (a2).

10. The cement of claim 1, wherein a total content of the photopolymerization initiator (c) is from 0.010 to 0.090 parts by weight, based on 100 parts by weight of the total amount of the polymerizable monomers (a1) and (a2).

11. The cement of claim 1, wherein a total content of the photopolymerization initiator (c) is from 0.020 to 0.080 parts by weight, based on 100 parts by weight of the total amount of the polymerizable monomers (a1) and (a2).

12. The cement of claim 1, wherein a total content of the photopolymerization initiator (c) is from 0.030 to 0.080 parts by weight, based on 100 parts by weight of the total amount of the polymerizable monomers (a1) and (a2).

13. The cement of claim 1, wherein the ratio, (c)/((d)+(e)), is from 1/27 to 1/12.

14. The cement of claim 1, wherein the ratio, (c)/((d)+(e)), is from 1/25 to 1/20.

15. The cement of claim 1, wherein the first and second compression modulus of the cured product are from 150 to 370 MPa and from 600 to 1500 MPa, respectively.

16. The cement of claim 1, wherein the first and second compression modulus of the cured product are from 200 to 350 MPa and from 750 to 1500 MPa, respectively.

17. The cement of claim 13, further comprising:
    a polymerization accelerator (f) in an amount of from 0.001 to 20 parts by weight, based on 100 parts by weight of a total amount of the polymerizable monomers (a1) and (a2).

18. The cement of claim 17, wherein the polymerization accelerator (f) is at least one selected from the group consisting of ethyl 4-N,N-dimethylaminobenzoate ester, methyl 4-N,N-dimethylaminobenzoate ester, n-butoxyethyl N,N-dimethylaminobenzoate ester, 4-N,N-dimethylaminobenzophenone, sodium benzenesulfinate, sodium p-toluenesulfinate, sodium 2,4,6-triisopropylbenzenesulfinate, sodium sulfite, potassium sulfite, calcium sulfite, ammonium sulfite, sodium hydrogensulfite, and potassium hydrogensulfite.

* * * * *